United States Patent [19]
Matsukawa et al.

[11] Patent Number: 5,871,948
[45] Date of Patent: Feb. 16, 1999

[54] ALKALINE REAGENT SOLUTION FOR ELIMINATING AMMONIA IN AN ASSAY

[75] Inventors: Hirokazu Matsukawa; Tuyosi Fujita, both of Osaka-fu; Tairo Oshima, Tokyo, all of Japan

[73] Assignee: Oriental Yeast Co., Ltd., Tokyo, Japan

[21] Appl. No.: 667,144

[22] Filed: Jun. 20, 1996

[30] Foreign Application Priority Data

Jun. 22, 1995 [JP] Japan .................................... 7-177955

[51] Int. Cl.⁶ .............. C12Q 1/26; C12Q 1/32; C12N 9/02; C12N 9/04
[52] U.S. Cl. .............. 435/26; 435/25; 435/189; 435/190; 435/822; 435/966
[58] Field of Search ................. 435/25, 26, 189, 435/822, 966, 190

[56] References Cited

U.S. PATENT DOCUMENTS

| | | | |
|---|---|---|---|
| 4,742,001 | 5/1988 | Marui et al. | 435/26 |
| 5,258,286 | 11/1993 | Marui et al. | 435/26 |
| 5,336,608 | 8/1994 | Niimura et al. | 435/189 |

FOREIGN PATENT DOCUMENTS

| | | |
|---|---|---|
| 0207493 | 1/1987 | European Pat. Off. . |
| 63-214182 | 9/1988 | Japan . |

OTHER PUBLICATIONS

Danson, M.J. and Wood, P.A. Isocitrate dehydrogenase of the thermoacidophilic archaebacterium *Sulpholobus acidocaldarius*, FEBS Lett., 172:289–293, 1984.
Fujita, T., Takata, S. and Sunagara, Y. Enzymatic rate assay of creatinine in serum and urine, Clin. Chem. 39:2130–2136, 1993.
Abstract of Japan, JP–A–02 255 098, Oct. 15, 1990.
Abstract of Japan, JP–A–63 214 182 Sep. 6, 1988.
Fossati et al, "A step forward in enazymatic measurement of creatinine", Clinical Chemistry, vol. 40, No. 1 1994, pp. 130–137.
Chemical Abstracts (1984) 100:188433d cited in the examination of USSN 06/878561 which is the original USSN of US Patent No. 5,258,286.

*Primary Examiner*—David M. Naff
*Assistant Examiner*—Janet M. Kerr
*Attorney, Agent, or Firm*—Browdy and Neimark

[57] ABSTRACT

The invention relates to an ammonia elimination reagent for use in an enzymatic assay of a biological substance which produces ammonia as the reaction product. The reagent is an alkaline solution of pH 9 to 11 and contains Sulfolobus-derived thermostable isocitrate dehydrogenase, 2-oxoglutaric acid, a reducing coenzyme, isocitric acid, glutamate dehydrogenase, and a divalent metal salt. The reagent can be stored in solution and has excellent stability under conditions of alkaline pHs.

5 Claims, 5 Drawing Sheets

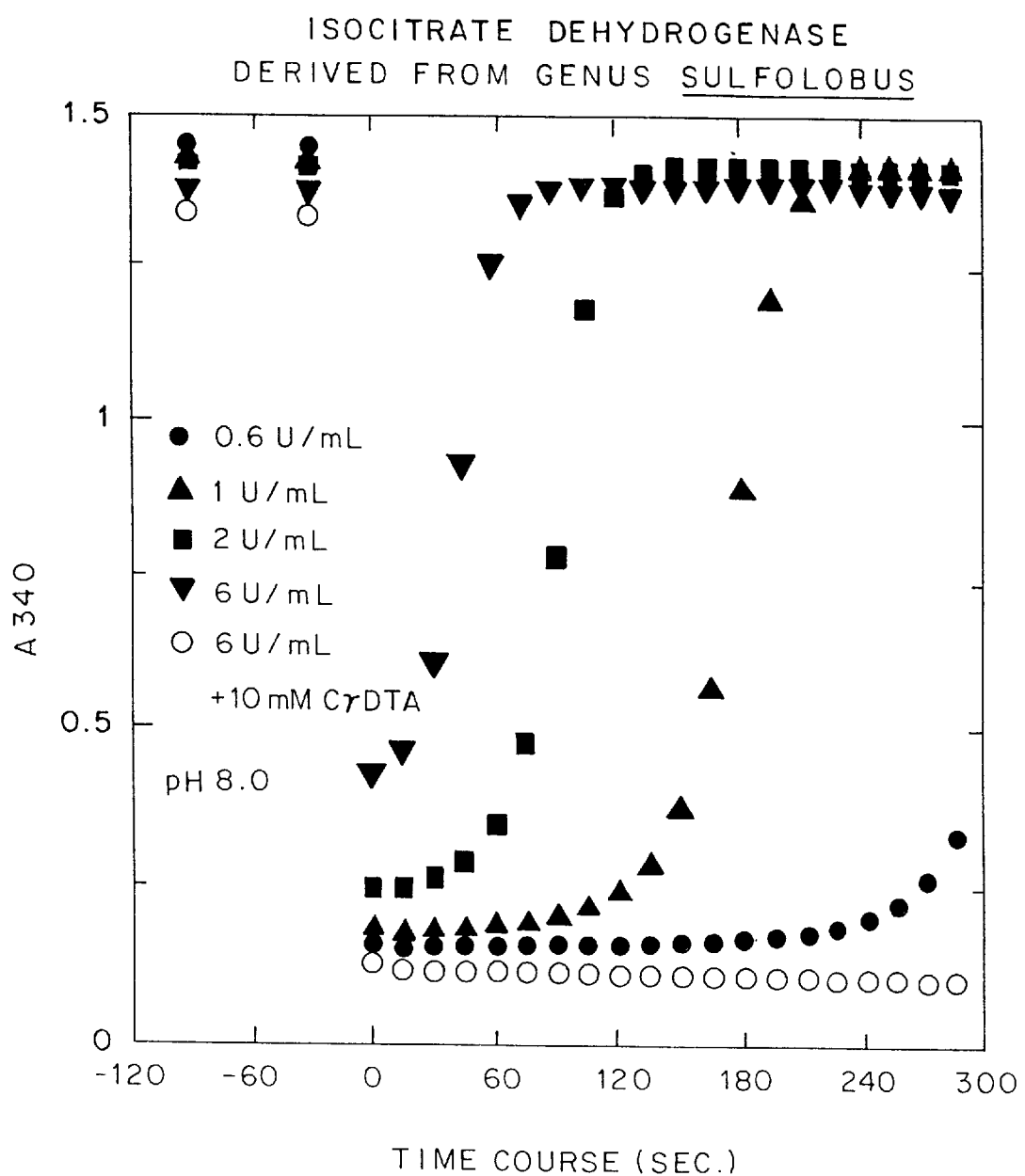

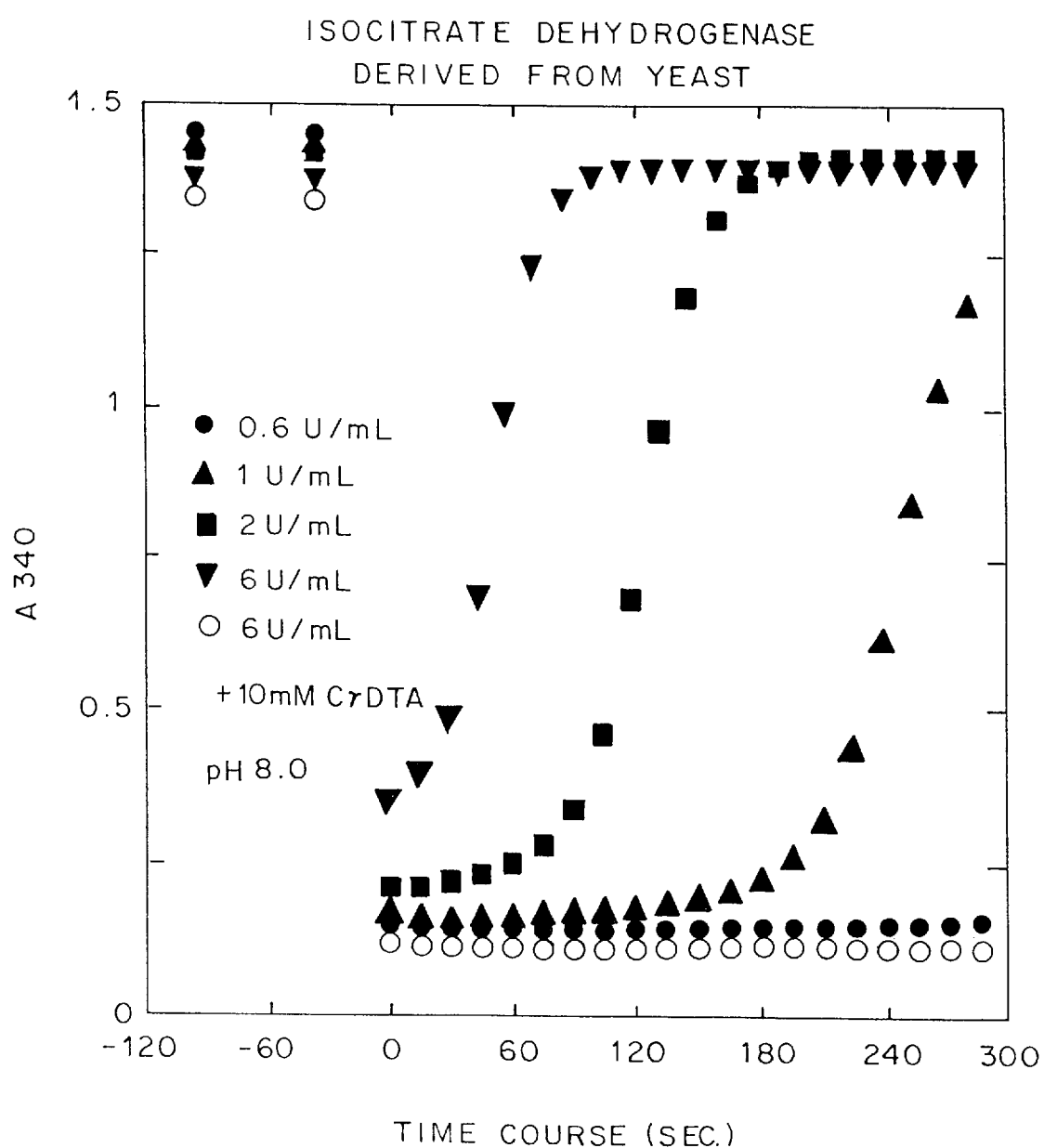

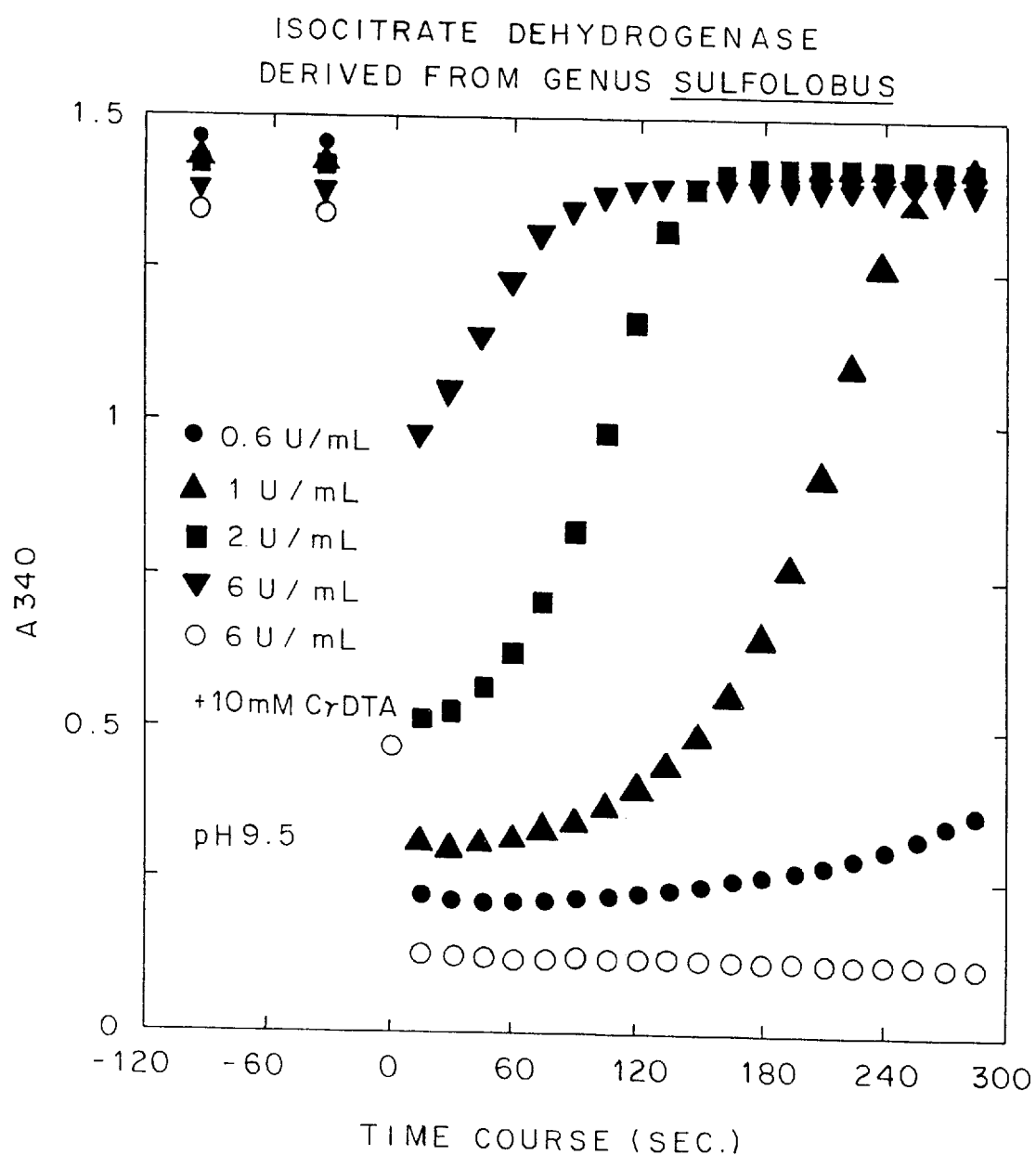

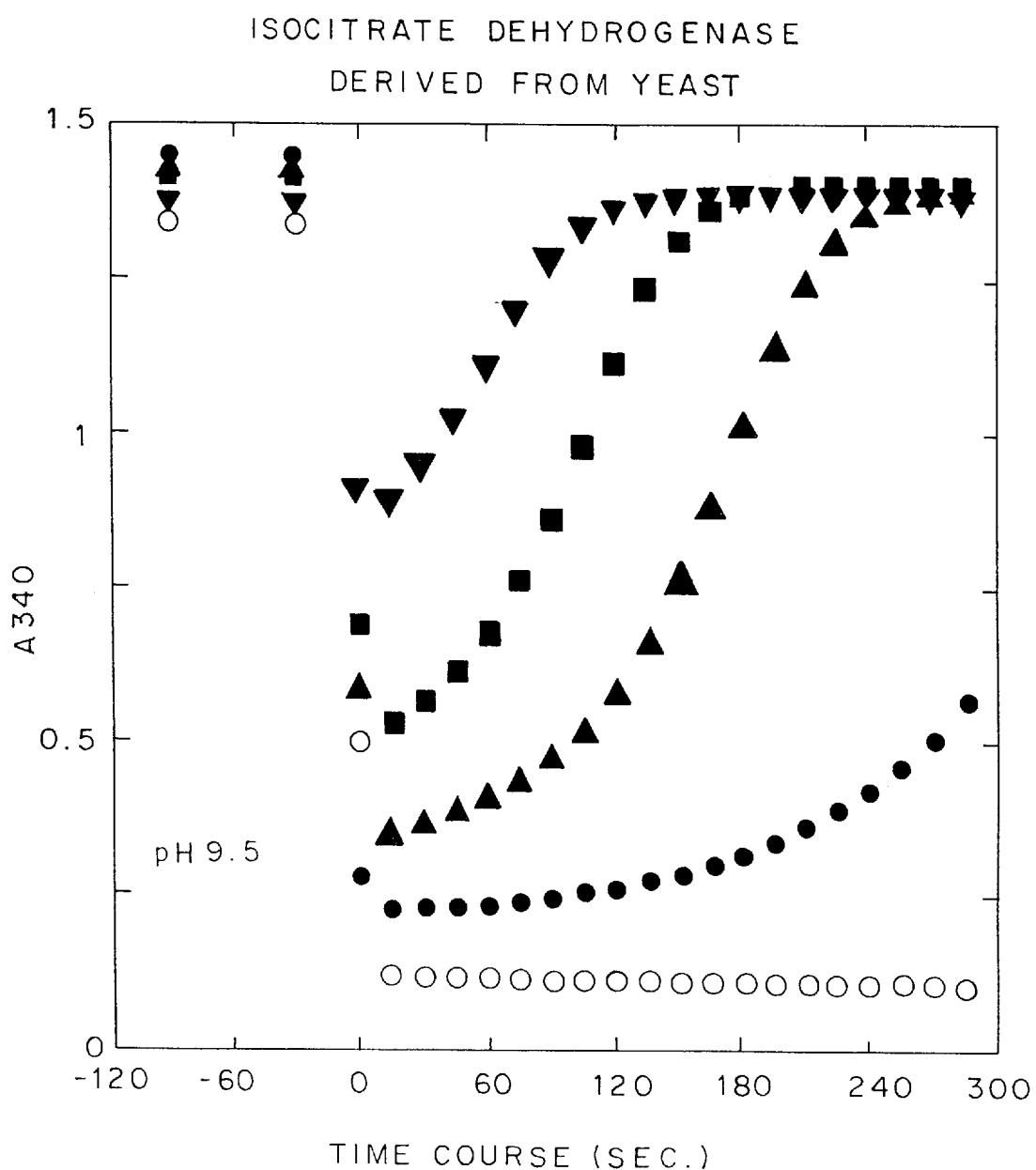

ALKALINE REAGENT SOLUTION FOR ELIMINATING AMMONIA IN AN ASSAY

BACKGROUND OF THE INVENTION

1. Field of the Invention

The present invention relates to an enzymatic assay method of a biological substance producing ammonia as the reaction product, wherein ammonia present in a sample of the biological substance is preliminarily consumed so as to accurately assay such substance, and also relates to an ammonia elimination reagent for enzymatic assay method using a thermostable isocitrate dehydrogenase as a coupling enzyme, the dehydrogenase being preferred for a reagent in solution and having excellent stability at alkaline pHs.

2. Description of the Prior Art

Generally, detection of substances in urine, blood serum and the like, including urea, creatinine, creatine, guanine and adenosine is routinely conducted. Also, the activities of various enzymes in relation with these substances are assayed. For the detection of such substances and the enzymatic reactions thereof, ammonia is initially generated, and the resulting ammonia is then converted into glutamic acid via glutamate dehydrogenase (abbreviated as "GLD" hereinafter) to determine at 340 nm the reduction of NAD(P)H via the coupled reaction: the reduction-type nicotine amide adenine dinucleotide (phosphate) [NAD(P)H] →nicotine amide adenine dinucleotide (phosphate) [NAD(P)$^+$].

Because ammonia is measured as a reaction product in the reaction system, however, ammonia originally present in a sample is also measured and included in the measured value. Therefore, it has been difficult to accurately assay such substances. Thus, ammonia present in a sample should be pretreated with 2-oxoglutaric acid via GLD to be converted to glutamic acid. Because the reaction system ammonia→glutamic acid involves the change of NAD(P)H→NAD(P)$^+$, the generated NAD(P)$^+$ should be again converted into NAD(P)H through the reverse reaction NAD(P)$^+$→NAD(P)H. Then, a coupled reaction can be induced by isocitrate dehydrogenase using as the substrate isocitric acid, together with metal ions such as magnesium ion or manganese ion. The reaction scheme is shown in FIG. 1.

SUMMARY OF THE INVENTION

A great number of diagnostic reagents are likely to be prepared in solution in place of freeze-dry powder in recent years, to minimize the difficulty in conducting a vast number of diagnostic laboratory tests by eliminating the process of dissolving a powdery reagent in a solution each time the reagent is to be used. However, in reagent in solution has a problem such that assay reagents containing NAD(P)H which are stable under alkaline conditions are readily inactivated because of the presence of conventional isocitrate dehydrogenase from yeast that it is very difficult to ensure the long storage life of such reagents. Hence, no satisfactory reagents in solution have been produced yet.

BRIEF DESCRIPTION OF THE DRAWINGS

FIG. 2A and 2B are graphs depicting the ammonia elimination activities Of the iCDH from genus Sulfolobus (FIG. 2A) and of the iCDH from yeast (FIG. 2B), in alkaline pH (pH 8.0); and FIG. 3A and 3B are graphs depicting the ammonia elimination activities of the iCDH from genus Sulfolobus (FIG. 3A) and of the iCDH from yeast (FIG. 3B), in alkaline pH (pH 9.5).

DETAILED DESCRIPTION OF THE INVENTION

Figure 1:
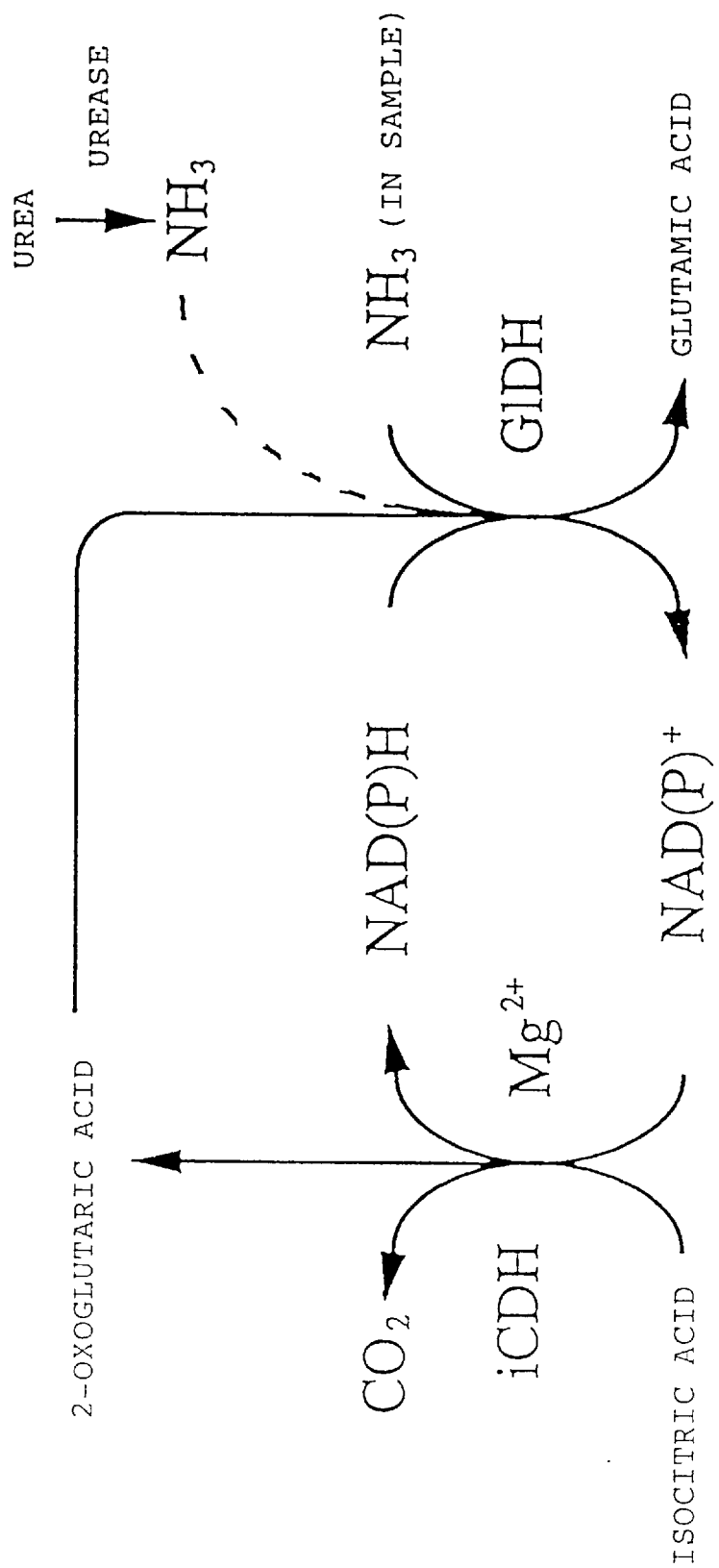
FIG. 1 depicts the scheme of the reaction pathway of ammonia elimination.

The present inventors have made investigated isocitrate dehydrogenase in view of such conventional problems. Consequently, the inventors have found that the isocitrate dehydrogenase (referred to as "iCDH" hereinbelow) from acidophilic, thermostable bacteria of genus Sulfolobus is thermally resistant and highly stable under alkaline conditions. The present inventors have furthermore found that reagents containing NAD(P)H in solution can be stored for a long period of time, by using the iCDH described above in an assay system of a biological substance which produces ammonia as a reaction product. Thus, the present invention has been achieved.

The present invention relates to an agent for eliminating ammonia in solution, containing 2-oxoglutaric acid, a reduction-type coenzyme (preferably, NADPH), isocitric acid, glutamate dehydrogenase, and isocitrate dehydrogenase as the reagent components, and being stable under alkaline pH conditions for a long period of time. Additionally, the present invention relates to an assay method of a biological substance which produces ammonia as the reaction product, comprising consuming the ammonia present in a sample of the biological substance, subsequently adding a chelating agent to the sample to terminate the iCDH reaction, and adding simultaneously or thereafter an enzyme which produces ammonia as a reaction product to assay the generated ammonia.

In accordance with the present invention, the bacteria of genus Sulfolobus are acidophilic, thermostable bacteria; as such bacteria, use may be made of *acidocaldarius, brierleyi, solfataricus* and other bacterial strains of genus Sulfolobus. The standard bacterial strains include a bacterial strain of *Sulfolobus acidocaldarius,* listed in catalog under DSM 639 (IFO 15157) and a bacterial strain of *Sulfolobus solfataricus,* listed in catalog under DSM 1616 (IFO 15331 (the old No. IFO 15158)). Strains DSM 639 and DSM 1616 were deposited under the terms of the Budapest Treaty in The National Institute of Bioscience and Human-Technology, Agency of Industrial Science and Technology, Ministry of International Trade and Industry of 1–3, Higashi 1 chome, Tsukuba-shi, Ibaraki-ken, 305, Japan under Nos. FERM BP-5567 and FERM BP-5566 respectively, on Jun. 14, 1996.

The extraction and purification of iCDH relating to the present invention are conducted on the basis of known findings. In accordance with the present invention, the procedure was carried out according to the method described in Japanese Patent Laid-open No. Sho 63-214182 (i.e., JP-A 63-214182 (1988)). Furthermore, the iCDH of the present invention may be recovered by extracting the enzyme from the cultured bacteria of genus Sulfolobus and purifying the enzyme. Otherwise, the iCDH may be a recombinant type, which is generated by inserting a DNA vector having genetic information of the iCDH from genus Sulfolobus into a bacterial strain and recovering the iCDH generated from the transformed bacterial strain. As the host bacteria, then, use may be made of for example, *Escherichia coli,* yeast, Actinomyces, *Bacillus subtilis,* and the like.

In accordance with the present invention, the reducing coenzyme includes NADH, NADPH, ATP and the like and the derivatives of these reducing coenzymes including thio-NADH (thionicotine amide adenine dinucleotide), thio-NADPH (thionicotine amide adenine dinucleotide phosphate), APADPH (acetylpyridine adenine dinucleotide phosphate) and the like.

For preparing an agent for eliminating ammonia which is stable in solution, preference is given to a buffer solution having a buffering action around pH 9 to 11 because of the selection of alkaline pHs with respect to the stability of reduction-type coenzymes in solution, in particular. For example, the most appropriate buffers of various types are listed in the Catalog of Dojin Chemical Research Institute, 19-th edition, 1994; preferred buffers are triethanolamine, TAPS [N-tris(hydroxymethyl)methyl-3-aminopropane sulfonic acid], CHES (N-cyclohexyl-2-aminoethane sulfonic acid), CAPSO (N-cyclohexyl-2-hydroxy-3-aminopropane sulfonic acid), CAPS (N-cyclohexyl-3-aminopropane sulfonic acid) and the like.

Examples of the agents for eliminating ammonia using the iCDH from genus Sulfolobus are listed in the table below to show the agent components. For the preparation of the agent for eliminating ammonia, any buffer having an buffering action at alkaline pHs may satisfactorily be used. In the table, the activity of GLD is expressed as follows; an enzyme activity generating 1 μmol of $NADP^+$ per minute is defined as one unit. If necessary, furthermore, a surfactant such as Briji-35 may be added.

TABLE 1

Composition of Agent for Eliminating Ammonia (composition example)

| | |
|---|---|
| 2-Oxoglutaric acid | 6.4 mM |
| NADPH | 0.3 mM |
| Potassium isocitrate | 10 mM |
| GLD | 20 to 100 U/ml |
| iCDH | 1 to 10 U/ml |
| $MgCl_2$ | 0.2 mM |
| pH | 9 to 10 (preferably, 9.5) |

For preparation of the agent for eliminating ammonia, the other principal component GLD may be derived from yeast, genus Proteus and genus Bacillus. For preparation of the agent for eliminating ammonia, any GLD may be satisfactory, but preference is given particularly to GLD with good stability and higher activity of producing glutamic acid in an alkaline pH.

In accordance with the present invention, the method for assaying the enzyme activity of iCDH should be conducted as follows, unless otherwise stated.
Assaying temperature: 37° C.
Composition of reaction solution:
 0.1M Tris-HCl buffer, pH 8.5
 5.0 mM potassium isocitrate
 1.0 mM $NADP^+$
 5.0 mM $MgCl_2$
Detector: spectrophotometer of Type U-2000, manufactured by Hitachi, Co.
Calculation of enzyme activity : The absorbance at 340 nm was measured spectrophotometrically, to determine the absorbance change per minute to calculate the enzyme activity. One unit (1 U) is defined as the activity generating 1 μmol of NADPH/minute.

For the subsequent culturing and extraction of iCDH, the bacteria of *Sulfolobus acidocaldarius* DSM 639, FERM BBP-5567 were cultured under aeration in the culture medium of the components shown below in Tables 2 and 3, under the temperature conditions of 80° C. for 5 days.

TABLE 2

Culture medium composition

| | |
|---|---|
| Glucose | 1.00 g/1 liter |
| Yeast extract | 1.00 g |
| Casamino acid (manufactured by Difco. Co.) | 1.00 g |
| Ammonium sulfate | 1.30 g |
| $KH_2SO_4$ | 0.28 g |
| $MgSO_4.7H_2O$ | 0.25 g |
| $CaCl_2.2H_2O$ | 0.07 g |
| $FeCl_3.6H_2O$ | 0.02 g |
| Trace element (×1000 conc.) | 1.0 ml |

The components were sufficiently mixed together, to be then adjusted to pH 3.0 with sulfuric acid.

TABLE 3

Preparation of trace element (×1000 conc.)

| | |
|---|---|
| $MnCl_2.6H_2O$ | 1,800 mg per 1 liter |
| $Na_2B_4O_7.7H_2O$ | 4,500 mg |
| $ZnSO_4.2H_2O$ | 220 mg |
| $CuCl_2.2H_2O$ | 50 mg |
| $NaMoO_4.2H_2O$ | 30 mg |
| $VOSO_4.XH_2O$ | 30 mg |
| $CoSO_4$ | 10 mg |

Adding dropwise sulfuric acid, the elements were dissolved.

Collecting the bacteria by centrifuge prior to washing, the bacteria were then disrupted by ultrasonication to recover a bacterial extract solution to prepare iCDH. The enzyme activity of the prepared iCDH was assayed by the spectrophotometric method described above. As a result, the bacteria of a wet weight of 1 g corresponded to 1 U enzyme activity at 37° C.

From the bacteria cultured under the culture conditions described above, iCDH was recovered by the following procedures.

1. Preparation of bacterial extract solution

An extracting buffer in an amount of ten times by weight of that of the bacteria was added to the bacteria to prepare a bacterial suspension, and the suspension was stirred at ambient temperature for 30 minutes while adjusting the suspension to pH 7.5 using 5N NaOH. The resulting solution of the disrupted bacteria was centrifuged at 8,000 rpm for 20 minutes (using a rotor of Type Therval GS3, manufactured by Dupont Co. Ltd.), and after discarding the precipitate, the supernatant was prepared as a bacterial extract solution.

| | |
|---|---|
| Extracting buffer: | 10 mM Tris-HCl buffer, pH 7.5 |
| | 1.0 mM EDTA |
| | 0.2 mM PMSF |
| | 0.02% sodium azide. |

2. Ion exchange chromatography using DEAE-Sepharose CL6B gel

The bacterial extract solution was diluted 3 fold with pure water, and was then charged into a 5-liter column (DI, 25 cm×11 cmH) packed with DEAE Sepharose CL6B to recover the fraction passing through the ion exchange column as an iCDH-containing fraction.

Column equilibrating solution and washing solution:
 10 mM Tris-HCl buffer, pH 7.5
 1.0 mM EDTA
 0.02% sodium azide.

Conditions for ion exchange chromatography
Flow: 5 liters/hr
Fractionation: 1 hr/Frac.
3. Dye affinity chromatography using Blue-Sepharose CL6B gel The fraction passing through the DEAE-ion exchange column, as the starting material for iCDH purification, was fractionated by affinity chromatography using Blue-Sepharose CL6B. The iCDH bound into the dye affinity column was eluted on 0–0.3M KCl gradient.

Column equilibrating solution and washing solution:
  10 mM Tris-HCl buffer, pH 7.5
  1.0 mM EDTA
  0.02% sodium azide.

Conditions for affinity chromatography
Column size: DI 10 cm×6 cm H
Gel volume: 500 ml
Flow: 1 liter/hr
Elution: 0–0.3M KCl gradient elution in 10-fold-volume column
Fractionation: 200 ml/Frac.

4. Hydrophobic chromatography using Phenyl-Toyopearl 650 C resin

Adding ammonium sulfate to the iCDH solution recovered as the eluted fraction to a final concentration of 1.5M ammonium sulfate, the resulting mixture was then charged into a 100 ml column packed with a resin Phenyl-Toyopearl 650 C. Washing the column with an excess amount of 1.5M ammonium sulfate, pH 7.5 to remove unabsorbed substances, the iCDH fraction was collected on 1.5–0.5M ammonium sulfate gradient.

Column equilibrating solution and washing solution:
  10 mM Tris-HCl buffer, pH 7.5
  1.5M ammonium sulfate
  1.0 mM EDTA
  0.02% sodium azide.

Conditions for hydrophobic chromatography
Column size: DI 5 cm×6 cm H
Flow: 200 ml/hr
Elution: 1.5–0.5M ammonium sulfate gradient elution in 10-fold-volume column
Fractionation: 20 ml/Frac.

5. Gel filtration using TSK gel G3,000 SW column

Concentrating the purified iCDH fraction recovered in the above procedure 4 by using an Amicon ultrafiltration membrane, the concentrated fraction was then purified by HPLC on a column packed with TSK gel 3,000 SW to recover a stock solution of the purified enzyme.

| Eluate: | 0.5 M NaCl |
| --- | --- |
| | 10 mM potassium phosphate buffer, pH 7.0 |
| | 0.02% sodium azide |

HPLC conditions
HPLC system: CCPM, manufactured by TOSOH, Co. Ltd.
Column size: TSK gel G3,000 SW column (1 inch)
Flow: 3 ml/minute.

The general enzymatic performance of the thermo stable iCDH purified from *Sulfolobus acidocaldarius* DSM 639, FERM BP-5567 by the procedures described above is shown below.

Molecular weight: 82 kDa (by gel filtration), dimer.
Optimum pH: 8.0 (when the activity was assayed at 37° C.).

| Km for NADP$^+$: | 66 $\mu$M (pH 8.6, 37° C.) |
| --- | --- |
| | 42 $\mu$M (pH 9.5, 37° C.) |
| | 48 $\mu$M (pH 10.0, 37° C.) |

EXAMPLE 1

Using two types of iCDHs, namely commercially available iCDH from yeast (manufactured by Oriental Yeast Industry Co. Ltd.) and the iCDH from genus Sulfolobus (recovered by the purification method described above), comparative testing of ammonia elimination activity was conducted by mixing a sample, 100 mm $NH_4Cl$ (solution) with the agent solution (R1+R2) at a solution volume ratio of 10:300 as shown below.

First agent (R1) with various iCDH levels of 0.6, 1, 2, and 6 U/ml and with iCDH 6U/ml+10 mM CyDTA, were prepared. yDTA means trans-2,3-cyclohexanediamine-N,N,N',N'-tetraacetic acid.

The absorbance change was analyzed over time at 340 nm by an automatic analyzer (Cobas Fara) The compositions of the agents for eliminating ammonia and the conditions are shown below.

Conditions of agents for eliminating ammonia:
  Agent mixing ratio: S:DW:R1:R1=10:5:240:60 (in 1 mL). In the above, S means sample and DW means distilled water.
  Sample (S): 100 mM $NH_4Cl$
  First agent (R1): 0.6–6 u/ml iCDH added (measured at 37° C.)
  Second reagent (R2): GLD (150 U/ml measured at 37° C.; manufactured by Toyobo, Co. Ltd.)
  Composition of reagent dissolving solution (for the first and second reagents)
    6.4 mM 2-oxoglutaric acid
    0.3 mM NADPH
    10 mM potassium isocitrate
    0.2 mM $MgCl_2$
    0.1% Briji-35
    0.1M Tris-ethanolamine-HCl buffer, pH 8.0 or 9.0.
  For CyDTA addition: 12.5 mM CyDTA added to the first reagent to a final 10 mM concentration.
  Temperature for analysis: 37° C.
  Detector: Cobas Fara (manufactured by Baxter, Co. Ltd.)

The ammonia elimination performance of the iCDHs from various origins was analyzed at pH 8.0 and 9.5.

The results indicate that the difference in performance is small at alkaline pHs.

EXAMPLE 2

An agent for eliminating ammonia of the following composition, based on the agent for eliminating ammonia composition in Example 1, was subjected to storage and stability tests in alkaline pHs adjusted by a variety of buffers. To a final concentration of 0.2 U/ml, commercially available iCDH from yeast (manufactured by Oriental Yeast Industry Co. Ltd.) and iCDH from genus Sulfolobus (recovered by the purification method described above) were independently added to the reagent composition. The prepared reagents were stored at 4° C. and 37° C. for 11 days for testing the stability. The results are shown in Table 4.

Composition of agent for eliminating ammonia:

| | |
|---|---|
| 2-oxoglutaric acid | 6.4 mM |
| NADPH | 0.3 mM |
| potassium isocitrate | 10 mM |
| MgCl$_2$ | 0.2 mM |
| Briji-35 | 0.1%. |

So as to calculate the residual activity ratio of iCDH under conditions of various pHs and temperatures the activity immediately after the dissolution of the enzyme iCDH was defined 100%. The residual activity ratio of the iCDH from yeast was 77% on day 11 when stored at a higher pH, ie. pH 9.0 and 4° C. No significant decrease of the activity of the iCDH from genus Sulfolobus was observed, which indicates that the enzyme can be stored stably under conditions of alkalin pHs for a long period of time.

TABLE 4

Storage stability of a variety of agent for eliminating ammonia solution samples

| Sample No. | Buffer type (pH) | from yeast | | from Sulfolobus | |
|---|---|---|---|---|---|
| | | 4° C. | 37° C. | 4° C. | 37° C. |
| 1 | CHES (pH 9.0) | 44.4% | 14.8% | 100.0% | 100.0% |
| 2 | Bicine (pH 9.0) | 59.2 | 3.7 | 93.4 | 96.8 |
| 3 | TAPS (pH 9.0) | 77.8 | 37.0 | 96.8 | 100.0 |
| 4 | CHES (pH 9.5) | 25.9 | 0.0 | 87.5 | 87.5 |
| 5 | CAPSO (pH 9.5) | 44.4 | 3.7 | 93.4 | 93.4 |
| 6 | triethanolamine (pH 9.5) | 55.6 | 7.4 | 100.0 | 93.4 |
| 7 | CAPS (pH 10.0) | 11.1 | 0.0 | 96.8 | 84.3 |
| 8 | CHES (pH 10.0) | 11.1 | 0.0 | 93.4 | 81.3 |
| 9 | CAPSO (pH 10.0) | 13.0 | 0.0 | 90.6 | 84.4 |
| 10 | triethanolamine (pH 10.0) | 40.7 | 1.9 | 93.4 | 84.3 |

The pH adjustment of buffers was done at 25° C. Table 4 shows the ratio of the residual iCDH activity to the initial activity of iCDH added, under various storage conditions.

Effect of the invention:

In accordance with the present invention, an agent for eliminating ammonia which can be readily prepared into a reagent in solution and can be stored in a stable manner for a long period of time, using the iCDH from genus Sulfolobus. The iCDH has greater stability under conditions of alkaline pHs for the agent for eliminating ammonia than conventional compositions containing iCDH.

What is claimed is:

1. An agent for eliminating ammonia in an assay in the form of an alkaline solution of pH 9 to 11, comprising 2-oxoglutaric acid, a reducing coenzyme, isocitric acid, glutamate dehydrogenase, a salt of a divalent metal, and isocitrate dehydrogenase produced by a microorganism belonging to the genus Sulfolobus.

2. An agent for eliminating ammonia according to claim 1 wherein the microorganism is selected from the group consisting of *Sulfolobus solfataricus* FERM BP-5566 and *Sulfolobus acidocaldarious* FERM BP-5567.

3. An agent for eliminating ammonia according to claim 1 wherein the divalent metal is magnesium.

4. An agent for eliminating ammonia according to claim 1 wherein the reducing coenzyme is NADPH.

5. An agent for eliminating ammonia according to claim 1, wherein the alkaline solution has a pH of 9 to 10.

* * * * *